United States Patent [19]
Walters

[11] Patent Number: 5,460,800
[45] Date of Patent: Oct. 24, 1995

[54] LABELED FLUOROCARBON COMPOSITIONS

[75] Inventor: Mark A. Walters, San Diego, Calif.

[73] Assignee: Alliance Pharmaceutical Corp., San Diego, Calif.

[21] Appl. No.: 293,292

[22] Filed: Aug. 22, 1994

Related U.S. Application Data

[63] Continuation of Ser. No. 31,960, Mar. 16, 1993, abandoned.

[51] Int. Cl.$^6$ ......................................................... A61B 1/00
[52] U.S. Cl. .............................. 424/9.6; 424/9.8; 514/832
[58] Field of Search ........................ 424/9.6, 9.8; 514/832

[56] References Cited

U.S. PATENT DOCUMENTS

| | | | |
|---|---|---|---|
| 4,577,636 | 3/1986 | Spears | 128/654 |
| 4,762,701 | 8/1988 | Horan et al. | 424/1.1 |
| 4,783,401 | 11/1988 | Horan et al. | 435/34 |
| 4,865,836 | 9/1989 | Long, Jr. | 424/5 |
| 4,891,208 | 1/1990 | Janoff et al. | 424/1.1 |
| 4,951,673 | 8/1990 | Long | 128/653.1 |
| 4,987,154 | 12/1991 | Long, Jr. | 514/772 |
| 5,114,703 | 5/1992 | Wolf et al. | 424/5 |

FOREIGN PATENT DOCUMENTS

0272933A2  6/1988  European Pat. Off. .

OTHER PUBLICATIONS

Chowdhary RK, "Influence of fluorocarbon emulsions on porphyrin–sensitised oxidation of histidine" Photochem Photbiol (England), 51:4 Abstract Only (1990).

Rosenblum "Fluorocarbon emulsions and cerebral microcirculation" Federation Proceedings 34:6 pp. 1493–1498 (1975).

Haegel, et al. "Selective incorporation of dyes with fluorocarbon and hydrocarbon chains into coexisting micellar phases of sodium perfluoroctoate and dimethyl tetradecyl aminosice" Progr Colloid Polyum Sci 76: pp. 132–139 (1988).

Kolodgie, et al. "Limitation of No Reflow Injury of Blood–Free Reperfusion With Oxygenated Perfluorochemical" (Fluosol–DA 20%) JACC 189:1 pp. 215–223.

Azzolini, et al. "Interactions Between Light and Vitreous Fluid Substitutes" Arch. Opthamol. 110: pp. 1345–1347 (1992).

Mizuiri "Laparoscopic examination of primary biliary cirrhosis after administration of indocyanine green" Gastroenterol Endosc. (with English Summary) 28: pp. 769–777 (1986).

Reed, et al. "A fluorescent dye which recognizes mature peripheral erythrocytes of myeloproliferative disorders" Cell Biol. Int. Rep 11:1 pp. 55–62 (1977).

Del Buono, et al. "Relation Between the Organization of Spectrin and of Membrane Lipids in Lymphocytes" J. Cell Biol. 106: pp. 797–703 (1988).

Levitt, et al. "Perfluorinated fatty acids alter merocyanine 540 dye binding to plasma membranes" J. Toxic. and Env. Health, 20: pp. 303–316 (1987).

Lutz, et al. "Devenir dans l'organisme et influence fonctionnelle des fluorocarbures utiliséd comme transporterus d'oxygéne" Tomme XXIX, Revue Française de Transfusion et Immuno–Hématologie 6; pp. 443–453 (with English summary) (1986).

Lutz, et al. "Effects of Potential Blood Substitutes (Perfluorochemicals) on Rat Liver and Spleen" European Journal of Physiology 387:2 pp. 175–181 (1980).

Dorland's Medical Dictionary 27th Ed., p. 1845 (1988).

*Primary Examiner*—Gary E. Hollinden
*Attorney, Agent, or Firm*—Knobbe, Martens, Olson & Bear

[57] ABSTRACT

A composition for use in visualizing tissues comprising a physiologically-acceptable fluorocarbon liquid and a visualizable label such as a chromophore or visible or fluorescent dye associated therewith; preferably the fluorocarbon is in the form of an emulsion and the label has a lipophilic moiety. Also disclosed are methods for labeling and visualizing cells and tissue, such as those of the reticuloendothelial system.

7 Claims, No Drawings

LABELED FLUOROCARBON COMPOSITIONS

This application is a continuation of application Ser. No. 08/031,960, filed Mar. 16, 1993 abandoned.

FIELD OF THE INVENTION

The present invention relates to fluorocarbon compositions containing a visualizable label, and to their use in visualizing animal cells or tissues.

BACKGROUND OF THE INVENTION

Liquid fluorocarbons have a high affinity for oxygen and can dissolve or solubilize significant quantities of oxygen. For this reason, fluorocarbon emulsions have been used as biocompatible oxygen carriers and/or blood substitutes.

Fluorocarbon liquids have also been used as radiological imaging agents. See e.g., U.S. Pat. Nos. 3,975,512 and 4,987,154. Fluorocarbon liquids have also been used in magnetic resonance imaging. See e.g., U.S. Pat. No. 4,951,673.

In many instances it is desirable to directly visualize animal tissues or cells. Staining of tissues with tissue-specific dyes is a common histological technique. However, for certain tissues and cells, such as those reticuloendothelial (RES) system, there remains a need for better visualization techniques. A surgeon, for example, may use a radiological lymphographic technique to prepare presurgical films or pictures which indicate the location of lymphatic tissue in a patient. However, during surgery, working in the surgical incision, it may be more difficult to differentiate the tissue in question.

Similarly, in research applications, it is often desirable to identify and label certain tissues, such as RES tissues.

The present invention provides a ready mechanism for locating and visually identifying certain cells and tissues.

SUMMARY OF THE INVENTION

One aspect of the present invention is a fluorocarbon composition, comprising a Physiologically-acceptable liquid fluorocarbon, and a visualizable label associated with the fluorocarbon. The composition may further comprise an aqueous phase, and an emulsifier, wherein the composition is an emulsion and the liquid fluorocarbon comprises a fluorocarbon phase of the emulsion. In one embodiment, the label is a fluorescent label. Preferably, the label is hydrophobic and is associated with the fluorocarbon phase or with the emulsifier by lipophilic or hydrophobic interaction. The label may also be a visible dye.

The invention also includes a method for visualizing cells or tissue of an animal, comprising the steps of providing a fluorocarbon composition comprising a liquid fluorocarbon and a visualizable label associated therewith, administering the composition to the animal in vivo, permitting the composition to localize in cells or tissue, and visualizing the cells or tissue in which the fluorocarbon has localized. Preferably, the fluorocarbon composition is an emulsion and further comprises a continuous aqueous phase and an emulsifier, and the liquid fluorocarbon preferably comprises a discontinuous phase of the emulsion. In one embodiment, the discontinuous phase localizes in cells of the reticuloendothelial system. As above, the label may be fluorescent or may be a visible chromophore. The label is preferably hydrophobic and is associated with the discontinuous phase or the emulsifier by lipophilic or hydrophobic interaction. One particularly interesting use of this method is for visualizing lymph nodes or lymphatic vessels.

DETAILED DESCRIPTION OF THE INVENTION

The present invention utilizes fluorocarbons associated with a visualizable label, such as a visible or fluorescent dye or other chromophore, for marking tissues and cells. Unlike prior uses of fluorocarbons for radiographic, ultrasonic, or magnetic resonance imaging, the labelled fluorocarbons of the present invention may be directly visualized, with visible or ultraviolet light.

In one embodiment of the present invention, the fluorocarbon is in the form of a emulsion. Fluorocarbon emulsions are well known. Such emulsions comprise an aqueous phase, an emulsifier, and a fluorocarbon phase. Both oil-in-water and water-in-oil emulsions can be prepared. These emulsion may be prepared using known techniques. See, e.g., U.S. Pat. Nos. 4,987,154 and 4,865,836.

Suitable fluorocarbons for use in the present invention include any biologically compatible fluorocarbon. There are a number of fluorocarbons that have been disclosed for medical use. These fluorocarbons include his (F-alkyl) ethanes such as $C_4F_9CH=CH_4CF_9$ (sometimes designated "F-44E"), i-$C_3F_9CH=CHC_6F_{13}$ ("F-i36E"), and $C_6F_{13}CH=CHC_6F_{13}$ ("F-66E"), cyclic fluorocarbons, such as C10F18 ( "F-decalin," "perfluorodecalin" or "FDC"), F-adamantane ("FA"), F-methyladamantane ("FMA") , F-1, 3-dimethyladamantane ("FDMA") , F-di-or F-trimethylbicyclo[3,3,1]nonane ("nonane"); perfluorinated amines, such as F-tripropylamine ("FTPA") and F-tri-butylamine ("FTBA") , F-4-methyloctahydroquinolizine ("FMOQ") , F-n-methyl-decahydroisoquinoline ("FMIQ") , F-n-methyl-decahydroquinoline ("FHQ") , F-n-cyclohexylpurrolidine ("FCHP") and F-2-butyltetrahydrofuran ("FC-75" or "RM101").

Other fluorocarbons include brominated perfluorocarbons, such as 1-bromo-heptadecafluoro-octane ($C_8F_{17}Br$, sometimes designated perfluorooctylbromide or "PFOB"), 1-bromopentadecafluoroheptane ($C_7F_{15}Br$) , and 1-bromotridecafluorohexane ($C_6F_{13}Br$, sometimes known as perfluorohexylbromide or "PFHB"). Other brominated fluorocarbons are disclosed in U.S. Pat. No. 3,975,512 to Long. Also contemplated are fluorocarbons having nonfluorine substituents, such as perfluorooctyl chloride, perfluorooctyl hydride, and similar compounds having different numbers of carbon atoms.

Additional fluorocarbons contemplated in accordance with this invention include perfluoroalkylated ethers or polyethers, such as $(CF_3)_2CFO(CF_2CF_2)_2OCF(CF_3)_2$, $(CF_)_2CFO(CF_2CF_2)_3OCF(CF_3)$, $(CF_3)CFO(CF_2CF_2)F$, $(CF_3)_2CFO(CF_2CF_2)_2F$, $(C_6F_{13})_2O$. Further, fluorocarbon-hydrocarbon compounds, such as, for example compounds having the general formula $C_nF_{2n+1}C_{n'}F_{2n'+1}$, $C_nF_{2n+1}OC_{n'}F_{2n'+1}$, OR $C_nF_{2n+1}CF=CHC_{n'}F_{2n'+1}$, where n and n' are the same or different and are from about 1 to about 10 (so long as the compound is a liquid at room temperature). Such compounds, for example, including $C_8F_{17}C_2H_5$ and $C_6F_{13}CH=CHC_6H_{13}$. It will be appreciated that esters, thioethers, and other variously modified mixed fluorocarbon-hydrocarbon compounds are also encompassed within the broad definition of "fluorocarbon" materials suitable for use in the present invention. Mixtures of fluorocarbons are also contemplated. Additional "fluorocarbons" not listed here, but having those properties described in this disclosure are additionally contemplated.

The emulsifier used in preparing the emulsion may be any suitable material, such as pluronic, nonionic surfactant, any of the fluorinated surfactants, or phospholipid emulsifiers, such as lecithin. Egg yolk phospholipid is particularly preferred. The surfactant typically comprises from about 2% to about 8% of the emulsion, w/v, and the fluorocarbon comprises from about 5% or 10% to about 90%, 100%, or 125%, w/v. (Because their density is about 2, the weight percentage of fluorocarbon in the emulsion can exceed 100%.)

The visualizable label may be selected from a wide variety of known labels. The label used in the present invention may be selected from the large number of conventional dyes, pigments, chromophores, and the like. It is preferred that the dye is lipophilic, or that it at least contains a lipophilic moiety. Alternatively, the dye may contain a fluorophilic moiety, and in certain instances, may be a fluorocarbon.

The labels of the present invention, for example, may include the following known chromophores: nitroso groups, nitro groups, azo groups, disazo groups, trisazo groups, polyazo groups, azoic groups, such as nitrosamine and diazo amino groups, stilbene groups, diphenylmethane (ketone imine) groups, triarylmethane groups, naphthyl groups, xanthene groups, thiazole groups, azines, oxizines, thiazines, amino ketones, indigoid groups, thioindigoid groups, and the like. Fluorinated derivatives of the foregoing are also contemplated. Phosphorescent labels may be used. Many of the xanthene and naphthalene-type dyes are fluorescent. Fluorescein is a well known example.

One preferred category of fluorescent dye is disclosed in U.S. Pat. No. 4,783,401. These materials are long chain lipid-like cyanine compounds, which are commercially available from Zynaxis Cell Science, Inc., Melvern, Pa., under the trademark PKH-26™.

Although water soluble dyes may be used, such dyes remain largely in the aqueous phase and do not remain with the emulsion particles, except in the case of a water-in-fluorocarbon emulsion. On the other hand, the lipid-like labels such as those disclosed in U.S. Pat. No. 4,783,401 remain with the fluorocarbon droplet, apparently as a result of lipophilic or hydrophobic interaction with the surfactant or with the fluorocarbon.

Another group of labels which may be advantageously used in the present invention are fluorescent, fluorinated aromatic molecules. Such molecules include octafluoronaphthalene, which has a fluorescent emission maximum at about 354 nm at an excitation wave length of 339 nm. Other fluorinated aromatics which would be soluble in the fluorocarbon phase and which are expected to be highly fluorescent may also be used, such as F-pyrene and F-anthracene.

Additional suitable labels may be selected, for example, from those listed in the Sigma-Aldrich Handbook of Stains, Dyes and Indicators, F. J. Green (Aldrich Chemical Company, Milwaukee, Wis. 1990).

The fluorocarbons of the present invention may be used in cell culture applications, or more importantly, in vivo. Neat fluorocarbon containing the label may be introduced into the lungs or the gastrointestinal tract of an animal. Gastrointestinal administration may aid in visualization during surgical treatment of obstructions, for example. Fluorocarbon emulsions of the present invention may be administered intravenously, intraperitoneally, subcutaneously, or directly into a lymphatic vessel. In each instance, the labeled perfluorocarbon in the tissue in question may be utilized to label or visualize that tissue. Fluorocarbon emulsions tend to collect as a ring of enhancement around liver tumors, for example, 24 to 48 hours after IV administration. Fluorescent visualization of the fluorocarbon could facilitate surgical resection of such tumors. Moreover, it is contemplated that both fluorescent and visible dyes could be added to the same emulsion.

One particularly attractive method for using the technology of the present invention is in labeling the cells an organs of the RES system. Emulsified fluorocarbon materials tend to accumulate in RES organs such as the spleen and the lymph system. Moreover, fluorocarbon emulsions may be administered directly into lymphatic vessels (as in conventional lymphography). Alternatively, the lymphatic system, including vessels and lymph nodes, may be visualized by injecting fluorocarbon emulsion into tissues drained by the lymph nodes and vessels to be visualized. This technique is known as indirect lymphography. See, e.g., Wolf, et al, U.S. Pat. No. 5,114,703. It is believed that phagocytic cells such as lymphocytes pick up and internalize the fluorocarbon particles from the emulsion. These particles are transported through the lymphatic system where they accumulate in lymph nodes and in the spleen.

Imaging of lymph nodes, for example, is not only valuable in research applications; it is also of significant value in surgery. Often, biopsy or lymphectomy procedures are performed in which it is important to identify and remove the tissue in question. Removal of lymph nodes is desirable, for example, in surgical treatments of certain tumors. The ability to visualize the lymph nodes during such surgery (either directly or through fluorescence) is an important advantage of the present invention. It is of similar value in post surgical examination of tissue removed from the patient.

The invention may be more fully understood with reference to the following example:

EXAMPLE 1

Transport of Perfluorocarbon Emulsion From Subcutaneous Tissue to Regional Lymphatics A 60% w/v perfluhron emulsion (IMAGENT® LN, Alliance Pharmaceutical Corp., San Diego, Calif.) Was combined with a fluorescent cyanine dye having long chain lipid-like characteristics (PKH-26, Zynaxis Cell Science, Inc., Melvern, Pa.). In particular, a $10^{-3}$ M stock solution of PKH-26 was added to the perfluhron emulsion to provide a final concentration of PKH-26 of $10^{-5}$ M. The mixture was gently shaken in the dark for five minutes at room temperature (22° C.). Subsequently, the mixture was added to the same amount of fresh rabbit plasma and was gently mixed for one minute to stop the staining reaction. This suspension had a final concentration of 30% perfluhron, w/v. The resulting material was injected subcutaneously into the dorsal skin of the foot of anesthetized rabbits. Following injection, the foot was moved passively in a rotary direction at 0.3 Hz. Samples were collected from cannulated lower leg prenodal lymphatics over a period of two hours and were assayed for lymph flow rate, leukocyte count, and extracellular and intracellular labeled perfluorocarbon. Samples were taken at two hours, twenty four hours, and one week after injection. Following initial lymph sample collection, the foot was gently massaged for fifteen minutes and then the lymph measurements were repeated.

A fluorescent microscope was used to examine samples.

The intracellular flux of the perfluorocarhon was measured as a function of the fluorescence of the sample. The measured results were:

| | |
|---|---|
| 2 hours | $3.7 \pm 3.7 \times 10^{-6}$ µg/hr |
| 24 hours | $72 \pm 20 \times 10^{-6}$ µg/hr |
| 24 hours | $61 \pm 16 \times 10^{-6}$ µg/hr |

Extracellular flux was significantly greater at the initial stage:

| | |
|---|---|
| 2 hours | $1.5 \pm 0.4$ µg/hr |
| 24 hours | $0.25 \pm 0.07$ µg/hr |
| 1 week | undetectable |

Examination of afferent rabbit lymph fluid using fluorescence microscopy revealed both internalized PKH-26-stained perflubron particles and freely suspended perflubron particles. These features were not visible under brightfield examination of the same field.

What is claimed is:

1. A method for visualizing cells or tissue of an animal, comprising the steps of:

administering to said animal in vivo a highly fluorinated liquid fluorocarbon having a visible or fluorescent label associated therewith, and permitting said composition to localize in cells or tissue; and illuminating said cells or tissue with visible or ultraviolet light so as to visualize said cells or tissue in which said fluorocarbon has localized.

2. The method of claim 1, wherein said fluorocarbon composition is an emulsion and further comprises a continuous aqueous phase and an emulsifier, and wherein said liquid fluorocarbon comprises a discontinuous phase of said emulsion.

3. The method of claim 2, wherein said discontinuous phase localizes in cells of the reticuloendothelial system.

4. The method of claim 3, wherein said label is a fluorescent label.

5. The method of claim 3, wherein said label is a visible dye.

6. The method of claim 3, wherein said label is hydrophobic and is associated with said discontinuous phase or said emulsifier by lipophilic or hydrophobic interaction.

7. The method of claim 3, wherein lymph nodes or lymphatic vessels are visualized in said visualizing step.

* * * * *